(12) United States Patent
Stromsten et al.

(10) Patent No.: US 10,018,490 B2
(45) Date of Patent: Jul. 10, 2018

(54) FLOW METER FOR USE WITH A VENTILATOR

(71) Applicant: BREAS MEDICAL AB, Mölnlycke (SE)

(72) Inventors: Patrik Stromsten, Molnlycke (SE); Jan Hellberg, Marstrand (SE)

(73) Assignee: Breas Medical AB, Mölnlycke (SE)

( * ) Notice: Subject to any disclaimer, the term of this patent is extended or adjusted under 35 U.S.C. 154(b) by 0 days.

(21) Appl. No.: 15/122,198

(22) PCT Filed: Feb. 28, 2014

(86) PCT No.: PCT/EP2014/053988
§ 371 (c)(1),
(2) Date: Aug. 29, 2016

(87) PCT Pub. No.: WO2015/127994
PCT Pub. Date: Sep. 3, 2015

(65) Prior Publication Data
US 2016/0370213 A1    Dec. 22, 2016

(51) Int. Cl.
*G01F 1/38* (2006.01)
*G01F 1/36* (2006.01)
(Continued)

(52) U.S. Cl.
CPC ............ *G01F 1/386* (2013.01); *A61B 5/4836* (2013.01); *A61M 16/024* (2017.08); *A61M 16/206* (2014.02); *G01F 1/40* (2013.01); *G01F 1/44* (2013.01); *G01F 15/00* (2013.01); *A61B 5/0205* (2013.01); *A61B 5/02055* (2013.01); *A61M 2016/0027* (2013.01); *A61M 2016/0039* (2013.01); *A61M 2016/0042* (2013.01);
(Continued)

(58) Field of Classification Search
CPC . G01F 5/00; G01F 1/68; G01F 1/6845; G01F 1/6842; G01F 15/185; G01F 1/386; G01F 1/667; G01F 1/662; G01F 1/40; G01F 1/44; G01F 1/42
See application file for complete search history.

(56) References Cited

U.S. PATENT DOCUMENTS

| 5,529,093 A | 6/1996 | Gallagher et al. |
| 8,960,194 B2 * | 2/2015 | Cooke ................. A61M 16/20 128/204.18 |

(Continued)

FOREIGN PATENT DOCUMENTS

| DE | 102006046252 A1 | 4/2007 | |
| EP | 0552916 A1 * | 7/1993 | ............. A61B 5/087 |

*Primary Examiner* — Harshad R Patel
*Assistant Examiner* — Brandi Hopkins
(74) *Attorney, Agent, or Firm* — Ascentage Patent Law, LLC; Travis Lee Johnson; David S. Einfeldt

(57) ABSTRACT

A turbulator adapted to be mounted to or inserted in an inlet portion of a flow meter for a ventilator is disclosed. The turbulator is adapted to create a turbulent gas flow in the inlet portion downstream of the turbulator upon passage of a gas flow therethrough. A flow meter for a ventilator is provided. The flow meter may comprise such turbulator. The turbulator may be arranged in the inlet portion of the flow meter. A membrane for a ventilator flow meter is provided, as well as a flow meter comprising the membrane. A flow meter comprising a turbulator and a membrane is disclosed.

10 Claims, 7 Drawing Sheets

(51) Int. Cl.
 *G01F 1/40* (2006.01)
 *G01F 1/44* (2006.01)
 *G01F 15/00* (2006.01)
 *A61M 16/20* (2006.01)
 *A61B 5/00* (2006.01)
 *A61M 16/00* (2006.01)
 *A61M 16/10* (2006.01)
 *A61B 5/0205* (2006.01)

(52) U.S. Cl.
 CPC ............ *A61M 2016/103* (2013.01); *A61M 2016/1025* (2013.01); *A61M 2205/15* (2013.01); *A61M 2205/3375* (2013.01); *A61M 2205/502* (2013.01); *A61M 2206/14* (2013.01); *A61M 2230/04* (2013.01); *A61M 2230/10* (2013.01); *A61M 2230/14* (2013.01); *A61M 2230/18* (2013.01); *A61M 2230/205* (2013.01); *A61M 2230/30* (2013.01); *A61M 2230/432* (2013.01); *A61M 2230/435* (2013.01); *A61M 2230/50* (2013.01); *A61M 2230/60* (2013.01)

(56) References Cited

U.S. PATENT DOCUMENTS

| | | | |
|---|---|---|---|
| 9,737,677 B2* | 8/2017 | Grychowski | A61M 16/0057 |
| 2009/0007912 A1* | 1/2009 | Lindell | A61M 16/10 128/204.18 |
| 2012/0096948 A1 | 4/2012 | Laird et al. | |
| 2013/0312746 A1* | 11/2013 | Grychowski | A61M 16/208 128/203.14 |

* cited by examiner

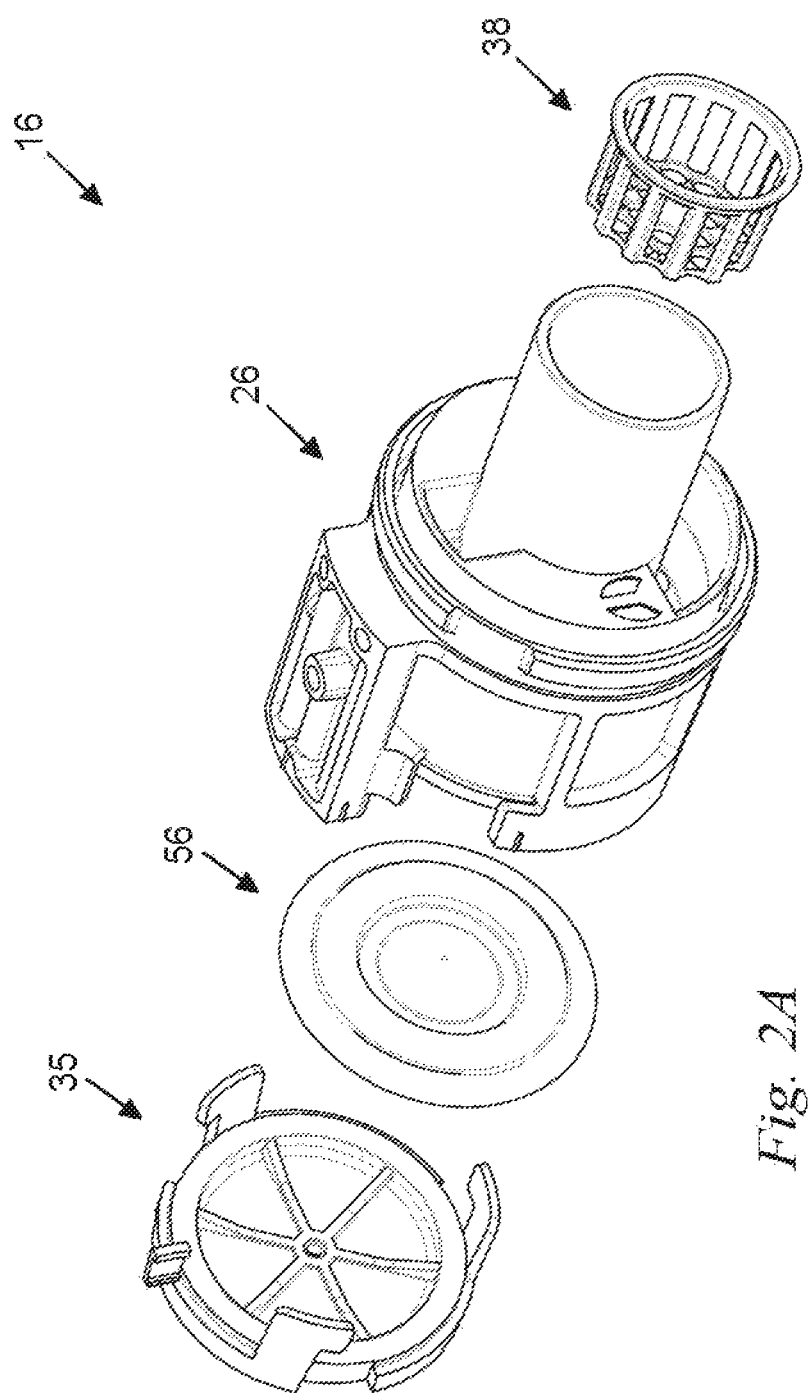

FLOW METER FOR USE WITH A VENTILATOR

TECHNICAL FIELD

The present invention relates to a flow sensor. In particular, it relates to a flow sensor for a mechanical ventilator.

BACKGROUND OF THE INVENTION

Patients suffering from different forms of breathing disorders can be subject to several types of treatments depending on the illness or disorder present. Such treatments include surgical procedures, pharmacologic therapy, and non-invasive mechanical techniques. Surgical techniques to remedy breathing disorders constitute a considerable risk for the patient and can lead to permanent injury or even mortality. Pharmacologic therapy has in general proved disappointing with respect to treating certain breathing disorders, e.g. sleep apnea. It is therefore of interest to find other treatments, preferably non-invasive techniques.

A mechanical ventilator represents a non-invasive technique for treatment of certain breathing disorders such as ventilatory failure, hypoventilation, and periodic breathing during sleep and awake and in sleep apnea that occurs exclusively during sleep. Ventilatory failure includes all forms of insufficient ventilation with respect to metabolic need whether occurring during wake or periods of sleep. Hypoventilation and periodic breathing, in its most frequently occurring form referred to as Cheyne-Stokes ventilation, may occur periodically or constantly during wake or sleep. Conditions associated with hypoventilation, in particular nocturnal hypoventilation include e.g. central nervous system disorders such as stroke, muscular dystrophies, certain congenital conditions, advanced chronic obstructive pulmonary disease (COPD), etc. Cheyne-Stokes ventilation or various forms of central apnea are commonly associated with cardiac and circulatory disorders, in particular cardiac failure.

Ventilatory failure is a potentially life threatening condition. The general comorbidity in patients with failing ventilation is considerable. The condition is highly disabling in terms of reduced physical capacity, cognitive dysfunction in severe cases and poor quality of life.

Patients with ventilatory failure therefore experience significant daytime symptoms but in addition, the majority of these cases experience a general worsening of their condition during state changes such as sleep. The phenomenon of disordered breathing during sleep, whether occurring as a consequence of ventilatory failure or as a component of sleep apnea in accordance with the description above causes sleep fragmentation. Daytime complications include sleepiness and cognitive dysfunction. Severe sleep disordered breathing occurring in other comorbid conditions like obesity, neuromuscular disease, post polio myelitis states, scoliosis or heart failure may be associated with considerable worsening of hypoventilation and compromised blood gas balance. Sleep apnea has been associated with cardiovascular complications including coronary heart disease, myocardial infarction, stroke, arterial hypertension, thrombosis, and cardiac arrhythmia. It is therefore of both immediate and long-term interest to reduce the exposure to sleep disordered breathing.

Recent advancement in mechanical non-invasive ventilator techniques includes administration of continuous positive airway pressure (CPAP) in different forms of sleep disordered breathing. During CPAP administration an elevated airway pressure is maintained throughout the breathing phase during a period coinciding with sleep. In sleep apnea this procedure may provide appropriate stabilization of the upper airway thereby preventing collapse. This, so called mono-level CPAP therapy, provides an almost identical pressure during inhalation and exhalation. Not only may CPAP be uncomfortable for the patient due to a sensed increased work of breathing during ventilation, specifically expiration. Some forms of apnea, mainly including those of central origin, and most forms of hypoventilation are only poorly controlled by CPAP. A more recently developed bi-level CPAP system administers different pressure levels during inhalation and exhalation. Bi-level CPAP provides increased comfort for most patients and not infrequently, an improved clinical response. Bi-level CPAP provides two pressure levels, Inspiratory Positive Airway Pressure (IPAP) and Expiratory Positive Airway Pressure (EPAP). IPAP is administered during the inhalation phase while EPAP is given during the exhalation phase.

In CPAP treatment it is crucial that the CPAP system complies with the patient's inspiratory and expiratory effort to make the treatment comfortable. A system that does not comply with patient efforts creates an air trapping situation and increase discomfort for the patient as well as considerably increasing the possibility of anxiety for the patient. One key component in such systems is the ability to sense the patient rhythm or breathing phases.

Flow systems, which succeeded the pressure systems, were based on a flow sensing mechanism which sensed the flow of gas entering and leaving the patient. There have been a number of methods of measuring the instantaneous and average gas flow described in literature to calculate the inspiratory and expiratory triggering points. The object of the invention is to overcome some of the deficiencies associated with known technology.

SUMMARY

One aim of the present disclosure is to improve the measurement accuracy of a flow meter. A flow meter with a low air flow resistance is presented.

One aim of the present invention is to provide a flow meter where the amount of noise is reduced. Different types of membrane arrangements contributing to minimizing vibrations during use are presented.

The present disclosure is partly based on the insight that, contrary to the prevailing assumption that gas flow through a gas flow meter should be laminar; a turbulent gas flow is advantageous for accuracy of flow measurement.

A flow meter is provided, especially a flow meter for a mechanical ventilator for the treatment of breathing disorders as described above. The flow meter is adapted for measuring the volume flow of gas leaving the patient. A turbulator adapted for use together with the flow meter is provided. Different types of membranes for the ventilator flow meter is provided. A ventilator comprising a flow meter, which in turn comprises either or both of the turbulator and the membrane is provided.

A turbulator is provided, which is adapted to be mounted to or inserted in an inlet portion of a flow meter for a ventilator. The turbulator may also be referred to as turbulation unit or turbulation device. The turbulator is adapted to create a turbulent gas flow in the inlet portion downstream of the turbulator upon passage of a gas flow there through. When a flow of gas entering the flow meter passes the turbulator, for example by passing through or passing by the turbulator, the gas flow is distributed such that a turbulent gas flow is created downstream of the turbulator. The gas flow is thereby not concentrated to the central portion of the tube, but is spread out also to the periphery of the tube. Thereby a substantially homogeneous flow velocity profile is obtained in the inlet portion, downstream of the turbulator.

In particular, the turbulator may be adapted for being mounted to or inserted in the inlet portion of a flow meter which will be described below. The inlet portion can be understood as being the first part of a flow channel, such as a tube, extending through the flow meter, allowing gas flow through the flow meter.

The turbulator may comprise a plate provided with a plurality of apertures, and the plate is adapted to be arranged across the inlet. The centre of the plate may be solid, or may comprise an aperture which is smaller than the plurality of aperture, which may further contribute to spreading the air flow within the tube. Preferably, the plate is adapted to be arranged substantially perpendicular to the direction of the intended gas flow.

The turbulator may comprise a hollow cylinder having a cylinder wall provided with a plurality of cylinder wall apertures and a plate arranged across one end of the cylinder, whereby the plate is provided with a plurality of plate apertures, the centre of the plate being solid. The plate may form the bottom part of the cylinder. The cylinder wall apertures may have elongated shape and the plate apertures may be circular, but other shapes may also be possible.

A flexible membrane for a flow meter, especially for a ventilator flow meter, is provided.

The membrane may comprise a central portion surrounded by a substantially flat rim portion forming a seal portion which is peripherally connected to a peripheral seal section via a spring suspension portion surrounding the rim portion. The spring suspension portion may comprise strengthening means adapted to provide the suspension portion with a spring constant such as to prevent resonant oscillations of the flexible membrane.

The flexible membrane may comprise a material having a rebound value lower than or equal to 35%, preferably lower than or equal to 33%, more preferably lower than or equal to 30%.

The membrane may comprise a material silicone material, such as a silicone 752, especially a silicone 752/50 material.

The membrane may comprise a material having a Shore hardness in the range of 35 to 55, preferably 50 Shore.

The membrane material may thereby be chosen such as to provide a high degree of damping of natural frequency vibrations, which may otherwise cause disturbing acoustic noise. A too low Shore hardness value will increase the tendency of the membrane to stick or cling to adjacent surfaces thereby obstructing the response of the membrane to pressure variations there over. A too high Shore hardness value, on the other hand, may lead to a slow response to pressure variations due to the resulting stiffness of the membrane.

The central portion may be cone shaped. The membrane material may thereby have a substantially constant thickness across the cone shaped portion.

By the specific geometry and/or the specific material, the membrane may be adapted to provide for fast response to pressure variations over the membrane. The membrane may be designed such that the influence of gravity upon the membrane is minimized, i.e., it should be stable in three dimensions when mounted in the flow meter, in order to provide for high accuracy of measurement results.

The spring suspension portion may comprise strengthening means adapted to provide the suspension portion with a spring constant such as to prevent resonant oscillations of the flexible membrane. Thereby, vibrations that might otherwise occur during use of the flow meter might be prevented, or at least decreased. Thereby, a noise level of the flow meter during use may be reduced comprised to a similar membrane without strengthening means. Further, the measurement accuracy may be increased.

Such strengthening means may comprise additional material, for example in the form of strengthening ribs, provided at specific locations on the membrane, specifically within the spring suspension portion. Such additional material may modify the spring constant of the spring suspension portion.

For example, strengthening means may comprise one or more elements extending in a radial direction in the spring suspension portion. Radial is supposed to be interpreted relative to the central portion of the membrane. These elements may be distributed around the circumference of the spring suspension portion.

Alternatively, the strengthening means may comprise one or more ring-shaped or segmented ring-shaped elements provided within the spring suspension portion, and encircling or at least partly encircling the central portion of the membrane. If a plurality of such ring-shaped or segmented ring-shaped elements are provided, they may be radially distributed within the spring suspension portion. Thereby, the ring-shaped or segmented ring-shaped elements may be located at different distances from the central portion of the membrane.

The spring suspension portion may be provided with weights, for example in the form of additional material at specific portions in order to minimize influence of gravity, and/or to function as balancing weights providing damping of natural frequency vibrations.

A flow meter is provided. The flow meter comprises a tube, having an inlet portion having a first inner diameter, an outlet portion having a second inner diameter, and an intermediate portion having a third inner diameter which is smaller than both the first inner diameter and the second inner diameter. The intermediate portion is located between the inlet portion and the outlet portion. A first pressure measuring point is located in the inlet portion and adjacent the intermediate portion, and a second pressure measuring point located in the intermediate portion. A turbulator may be arranged in the inlet portion of the flow meter. The turbulator may be a turbulator as described above.

The turbulator may be arranged in the inlet portion such that a gas flow entering the flow meter passes through, or by, the turbulator, whereby the gas flow downstream of the turbulator is turbulent. The gas flow may thereby be distributed over the cross section of the inlet portion. Thereby the gas flow velocity profile in a cross section of the tube downstream of the turbulator will be substantially continuous. The turbulator is preferably arranged in the inlet portion such that the flow velocity profile at the first pressure measurement point is substantially flat.

The pressure measurement points are locations intended for taking pressure measurements, based upon which parameters related to the flow may be deducted. Especially, the volume flow may be calculated. A pressure measurement point may comprise a port for connection to a pressure sensor, e.g. via a channel adapted to be connected to a pressure sensor. The first and the second pressure measuring points may thereby be connected to respectively each connection of a differential pressure sensor. Alternatively, an absolute pressure sensor might be connected to each of the pressure measurement points. The differential pressure sensor, or the absolute pressure sensors, may be located within the ventilator, but at some distance from the flow meter.

The flow meter may thus be a venturi type flow meter, comprising a tube having a narrowed, or waist-like, portion. The inlet portion is the portion of the channel extending from the inlet opening of the channel to the narrowed portion. The narrowed portion may be referred to as intermediate portion. The length of the inlet portion may be some multiples of the diameter of the narrowed portion.

The turbulator may comprise a plate provided with a plurality of plate apertures, wherein the plate is arranged across the inlet portion. The plate may be arranged substantially perpendicular to the intended direction of the gas flow upstream of the turbulator. The plate may be arranged substantially perpendicular to the inner walls of the inlet portion. The plate may be circular, with a size adapted to fit within the inlet portion of a flow meter.

The turbulator may comprise a hollow cylinder having a cylinder wall provided with a plurality of cylinder wall apertures and a plate arranged across one end of the cylinder, whereby the plate is provided with a plurality of plate apertures. The plate may form a bottom of the cylinder. The cylinder wall apertures may have elongated shape, preferably in a direction parallel to the cylinder axis, and the plate apertures may be circular. The plate apertures are preferably arranged such that a centre portion of the plate is solid. An annular space may be provided between the cylinder wall and the inner wall of the inlet portion. Thereby the gas may flow through the turbulator via both the cylinder wall apertures and the plate apertures.

When the turbulator comprises a plate with apertures, or a cylinder with apertures as previously described, these may be sized such as to prevent entry of undesired objects into the flow meter to which the turbulator is mounted. Such undesired objects may for example be objects comprised in the exhaust air, for example caused by phlegm or mucus or aggregations of phlegm or mucus. The turbulator may thus have a dual function of creating a turbulent gas flow downstream of the turbulator, and of functioning as a sieve or filter in order to minimize, or at least to some degree avoid, contamination of the interior of the flow meter. The size of the apertures is preferably such that entry of undesired objects is efficiently prevented while at the same time the apertures should not become clogged too quickly.

Providing a solid centre of the plate, or a centre of the plate provided with a minor aperture, located around the cylinder axis will block gas flow in the centre, which further contributes to creating a homogeneous flow velocity profile downstream of the turbulator.

The turbulator may be arranged in the inlet portion such that the plate is arranged at a distance from the tube inlet opening. If the turbulator comprises a cylinder as described above, it may be arranged in the inlet portion such that the plate, representing a bottom of the cylinder, is arranged at a distance from the opening of the inlet portion.

The tube may be arranged in a housing, the housing having a flow exhaust channel in flow connection to the outlet end, or outlet opening, of the outlet portion, the exhaust channel at least partly surrounding the tube. Thereby, the flow meter as described above may comprise a housing at least partly surrounding the tube. A pilot pressure chamber may be arranged adjacent to the outlet end of the outlet portion and adjacent to the exhaust channel, with a flexible membrane arranged between the pilot pressure chamber and the outlet of the outlet portion and the exhaust channel. The exhaust channel provides an exhaust for gas flow exiting the outlet portion, thereby leading the gas flow exiting the tube towards an exit of the flow meter. The pilot pressure chamber and the membrane are adapted such that the membrane, in a default position, substantially closes, or seals, or only leaves a relatively small opening in the connection between the outlet portion and the exhaust channel when pressure caused by the gas flow is lower than the pilot pressure provided in the pilot pressure chamber. The membrane is adapted to open the flow communication path between the outlet end and the exhaust channel in response to the gas flow through the tube and the pressure in the pilot pressure chamber. That is, the membrane is adapted to open and seal in response to the flow of exhaust gas from the patient, which, in turn, is determined by the ventilator fan.

The membrane may be a membrane as described above.

The membrane may comprise a central portion having a substantially flat rim portion forming a seal portion which is peripherally connected to a peripheral seal section via a spring suspension portion. The central portion may be flat or cone shaped. The membrane may be arranged in the flow sensor such that the central portion faces the outlet end of the outlet portion, the seal portion faces the borders of the outlet end, the spring suspension portion faces the exhaust channel, and the peripheral seal is arranged in sealing engagement between the housing and the pilot pressure chamber. The membrane may thereby have a substantially circular periphery. If the central portion is cone shaped, the cone tip is arranged such as to face the outlet portion.

The pilot pressure may be controlled such as to be varied according to the breathing cycle of the patient.

The membrane may be adapted such that when the pressure in the pilot pressure chamber is higher than the pressure in the outlet portion, the seal portion substantially seals against the borders of the outlet portion, or provides a minimum opening there between. When the pressure in the outlet portion is higher than the pilot pressure, the membrane flexes inwards towards the pilot pressure chamber via a flexing movement, especially via the spring suspension portion. Thereby, the resulting flow passage between the outlet portion and the exhaust channel has a large cross section, and the flow resistance is low, thereby providing low flow resistance through the flow meter. The spring constant of the spring suspension portion may be selected such as to optimize the response properties of the membrane to flow variations.

The membrane may be arranged such that an air flow resistance of a gas flow from the outlet end and into the exhaust channel will be lowest in a portion of the outlet end most distant from the second pressure measurement point. Thereby, the flow rate of air exiting the tube and entering the exhaust channel will be higher the further away from the second pressure measurement point the air flow rate is considered.

The flow measurement points may be located such that, when the flow meter is in the orientation in which it is intended to be used, the flow measurement points are located in the upper half of the tube. The portion of the outlet end most distance from the second flow measurement point may thereby be in the lower half of the outlet portion, when the flow meter is in the orientation in which it is intended for use.

The membrane may comprise a central portion having a substantially flat rim portion forming a seal portion which is peripherally connected to a peripheral seal section via a spring suspension portion, and the membrane may be arranged such that the seal portion faces the borders of the outlet end, the spring suspension portion faces the exhaust channel, and the peripheral seal is arranged in sealing engagement between the housing and the pilot pressure chamber.

The membrane may be arranged such that the distance between the seal portion and the borders of the outlet end is not constant throughout a circumference of the borders. The distance between the seal portion and the borders of the outlet end may be largest in a portion of the outlet end most distant from the second pressure measurement point. This may be achieved by arranging the membrane in the flow meter such that the membrane is tilted with respect to the outlet portion. Alternatively, or additionally, it may be achieved by a specific shape of the membrane and/or the outlet borders. For example, the borders of the outlet portion may be protruding more along one or more portions of their circumference than others.

The membrane may be represented by an average plane, which may be considered to comprise the planes of the flat rim portions. The tube, at least the outlet portion, may be represented by a cylinder having a cylinder axis. Tilting the membrane may then be considered as arranging the membrane such that a normal vector of this average plane forms an angle, larger than zero, with the cylinder axis.

The tube referred to above is an element defining a flow channel having an inlet portion having a first inner diameter, an outlet portion having a second inner diameter, and an intermediate portion having a third inner diameter which is smaller than both the first inner diameter and the second inner diameter. Alternatively, other constructions defining a flow channel having an inlet portion having a first inner diameter, an outlet portion having a second inner diameter, and an intermediate portion having a third inner diameter which is smaller than both the first inner diameter and the second inner diameter, are equally possible.

A ventilator is provided, comprising a flow meter according to any of the above embodiments.

BRIEF DESCRIPTION OF THE DRAWINGS (OPTIONAL)

In the following the invention will be described in a non-limiting way and in more detail with reference to exemplary embodiments illustrated in the enclosed drawings, in which:

FIG. 2A illustrates a perspective view flow meter according to some preferred embodiments;

DETAILED DESCRIPTION

In the following description, for purposes of explanation and not limitation, specific details are set forth, such as particular components, elements, techniques, etc. in order to provide a thorough understanding of the example embodiments. However, it will be apparent to one skilled in the art that the example embodiments may be practiced in other manners that depart from these specific details. In other instances, detailed descriptions of well-known methods and elements are omitted so as not to obscure the description of the example embodiments. The terminology used herein is for the purpose of describing the example embodiments and is not intended to limit the embodiments presented herein.

Figure 1A:
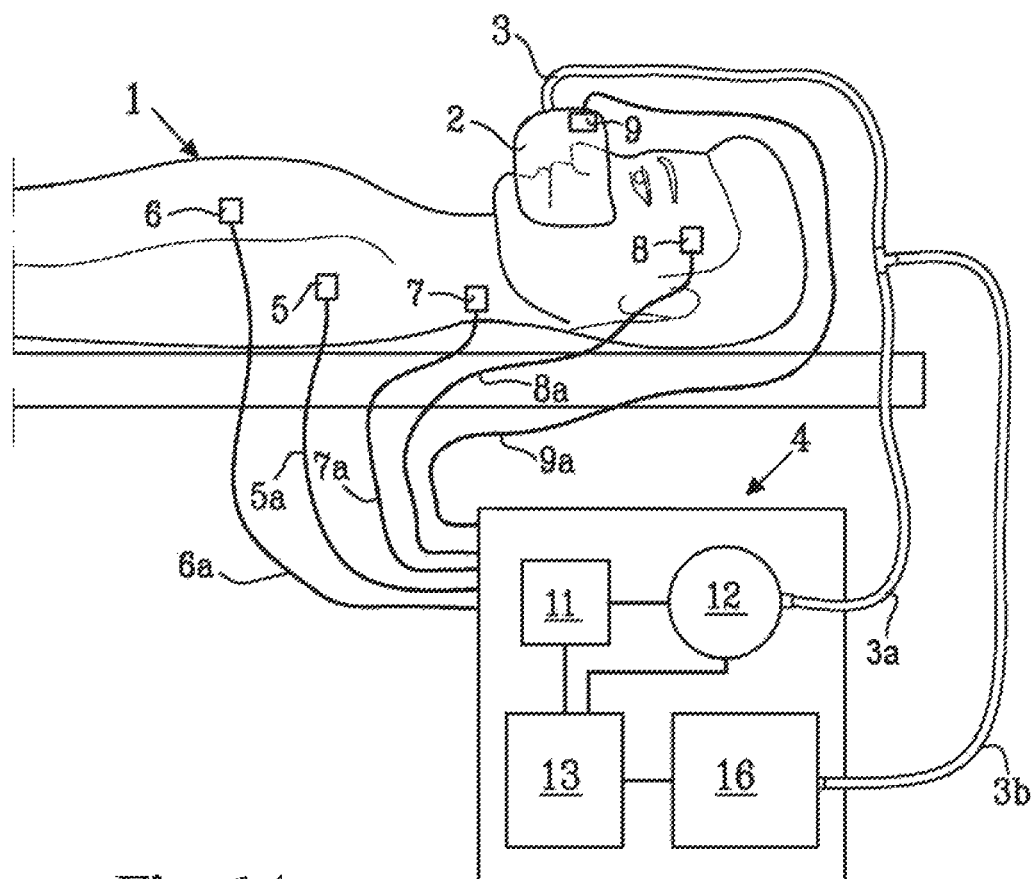
FIG. 1A, 1B illustrate a mechanical ventilation system.
Figure 1B:
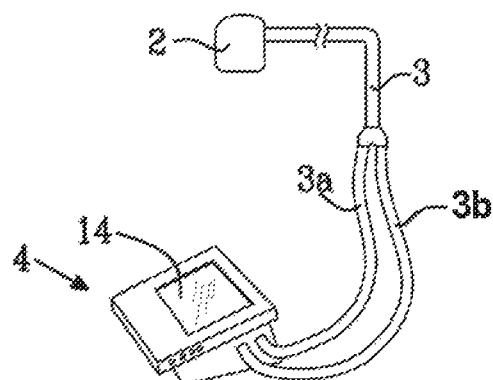

In FIGS. 1A and 1B a mechanical ventilation system used for the treatment of hypoventilation disorders is illustrated schematically. A ventilation system may comprise a mechanical ventilator 4 supplying pressurized breathing gas, tubing 3 for guiding breathing gas to and from the patient 1, a breathing mask 2 or similar for administrating the breathing gas to the patient 1, sensing means 5, 6, 7, 8, and 9 for determining the physiological status of the patient 1. A mechanical ventilator 4 is supplying breathing gas for instance as a positive airway pressure via a tubing 3a and through a mask 2 to a patient 1. The tubing 3 may comprise a tubing 3a for supplying breathing gas to the patient 1, and a tubing 3b, also referred to as exhaust gas tube, for guiding exhaust gas from the patient back to the ventilator 4. The mask 2 can be a face mask 2 covering both the mouth and nose or a nasal mask covering only the nose or nostrils depending on the patient's needs. It can also be a hood covering the complete head or body of the patient.

The ventilator 4 may comprise a source (not illustrated) of breathing gas or one or more components for breathing gas, and may be connected to means (not illustrated), such as a fan or blower for supplying breathing gas from the ventilator to the patient. The breathing gas may be of any suitable gas composition for breathing purposes as understood by the person skilled in the art, the composition depending on the physiological status of the patient.

The pressure or flow from the ventilator 4 delivered to the patient via tubing 3a may be measured by a flow meter 11 and/or a pressure sensor 12, which are controlled by a processing unit 13 as shown in FIG. 1. The processing unit 13 is configured to measure one or several input parameters 5, 6, 7, 8, and 9 obtained from the patient 1 describing the physiological status of the patient. Data indicative of patient status is obtained using sensors 5, 6, 7, 8, and 9 connected to the patient and transferred to the processing unit 13 via connection means 5a, 6a, 7a, 8a, and 9a. These input parameters may be for instance flow or pressure signals, data obtained from EEG, EMG, EOG, and ECG measurements, 02 and/or CO2 measurements in relation to the patient, body temperature, blood pressure, SpO2 (oxygen saturation), eye movements, and sound measurements. It should be understood that the invention is not limited to the above mentioned input parameters but other input parameters may be used. In FIG. 1 not all sensors 5, 6, 7, 8, and 9 and sensor connection means 5a, 6a, 7a, 8a, and 9a are depicted, only a subset is shown in order to illustrate a schematic view of the system and the depicted locations are only given as examples and are in no way limiting to the invention.

The ventilator device 4 may also have display means 14 for displaying measured data and obtained response parameters for use by a physician, other medical personnel, or the patient. The display means may be of any normal type as appreciated by a person skilled in the art. The data is displayed with such a high rate that a real time feedback is provided to a person monitoring the ventilator characteristics and function for immediate feedback and control.

The ventilator also comprises a second tubing 3b, here referred to as exhaust gas tube 3b, for guiding exhaust gas from the patient back to the ventilator 4. The exhaust gas tube may be connected to a flow meter 16 provided in the ventilator, in order to measure the exhaust gas flow. The flow meter 16 may be a flow meter according to any of the embodiments described herein. The flow meter 16 is, directly or indirectly, coupled to the processing unit 13. The flow meter 16 may be directly coupled to the processing unit 13 such as to provide measurement data concerning flow data to the processing unit, or it may be connected to processing unit 13 via one or more pressure sensors (not illustrated) which provide measurement data to the processing unit 13 for determination of flow data, e.g. volume flow. By comparing the inlet gas flow to the patient and the exhaust gas flow from the patient faults such as leaks within the system can be detected.

Figure 2B:
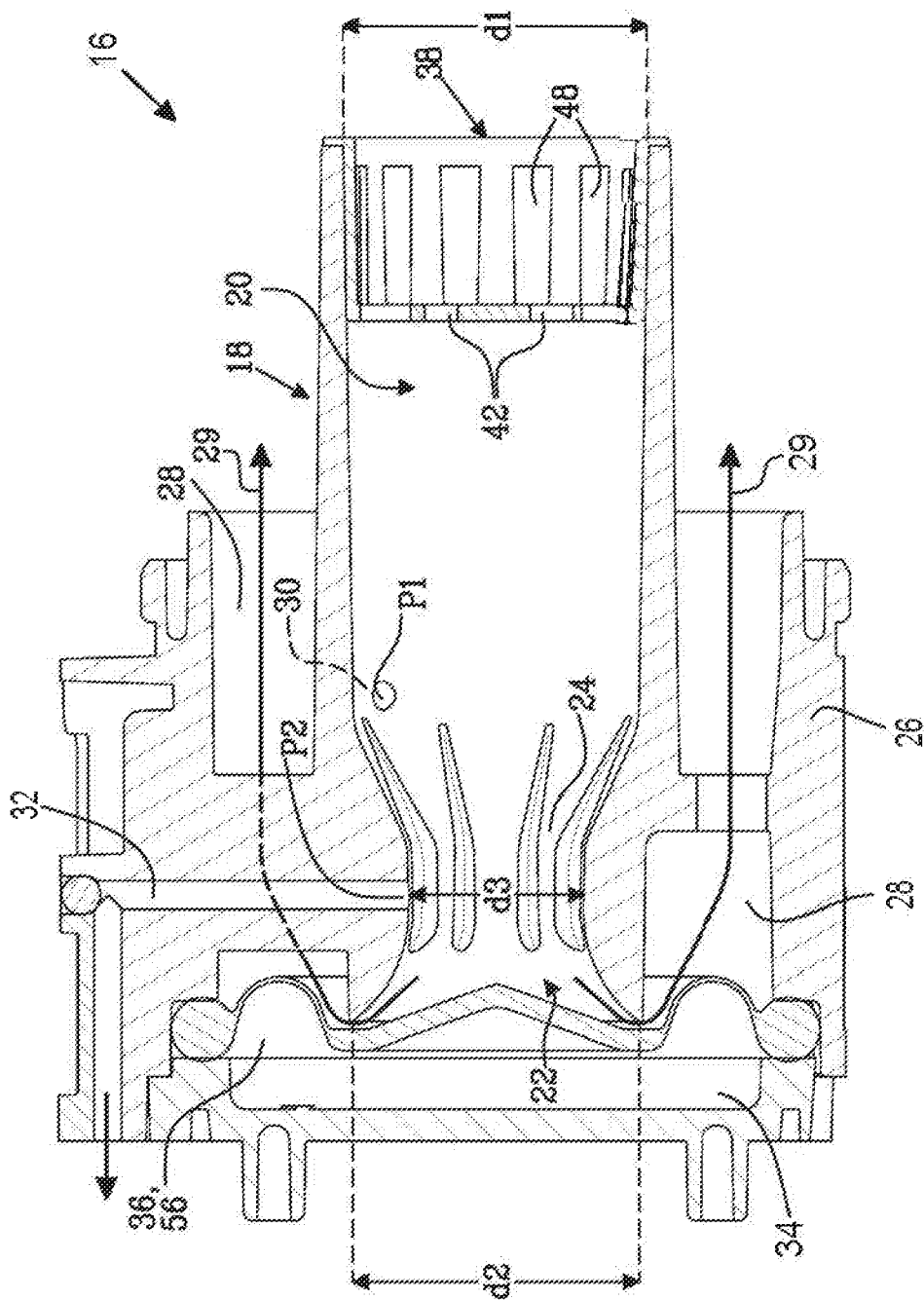
FIG. 2B illustrates a cross section of a flow meter according to some preferred embodiments.

A flow meter 16 according to some preferred embodiments is illustrated in an exploded perspective view in FIG. 2A and in more detail in FIG. 2B. The flow meter is based on the venturi principle, comprising a tube or similar, defining a flow channel having a narrowed, or waist-like, section. The volume flow through the flow meter can be calculated from pressure values obtained from pressure measurements upstream of the narrowest section and within the narrowest section. According to a general principle, the flow resistance through the flow meter should be as low as possible, in order to achieve high accuracy of the measurement. In the present flow meter, adapted to be used in ventilators of the type described above, high dynamical measurement accuracy is necessary, also during difficult conditions such as variations in the dimensions of the exhaust gas tubing 3b, bends in the tubing 3b, and high velocity of the gas flowing through the tube 3 and entering the flow meter.

In the example illustrated in FIGS. 2A and 2B, the flow meter 16 comprises a tube 18 having an inlet portion 20 having a first inner diameter d1, an outlet portion 22 having a second inner diameter d2, and an intermediate portion 24 having a third inner diameter d3 which is smaller than both the first inner diameter d1 and the second inner diameter d2. In order to minimize the space requirements, the outlet portion 22 of the tube 18 is shortened compared to conventional venturi flow meters. The tube 18 is at least partly surrounded by a housing 26, which is adapted to be mounted in a ventilator 4. In the illustrated example, a portion of the tube 18 extends out of the housing 26. The housing 26 comprises an exhaust channel 28 which is in fluid connection with the outlet portion 22. The exhaust channel 28 allows the gas flow 29 to escape out of the flow meter 16 and out of the ventilator 4. In the embodiment illustrated in FIGS. 2A and 2B, the exhaust channel 28 partly surrounds the tube 18.

The tube 18 is provided with two points P1 and P2 for pressure measurements. The first pressure measurement point P1 is located in the inlet portion 20, i.e. at a portion of the tube 18 having an inner diameter d1 but adjacent the intermediate portion 24 representing the waist-like section. The second pressure measurement point P2 is located within the intermediate portion 24, in its narrowest portion having an inner diameter d3. As described above, at these points ports or channels 30, 32 are provided for connection to pressure measurement means, for example a differential pressure sensor (not illustrated). The pressure measured at points P1 and P2 is transmitted to the processing unit 13. Based on the pressure values measured at P1 and P2 the volume flow through the flow meter may be determined. As illustrated in FIG. 2, the pressure measurement positions P1, P2 are located at the topmost part of the tube 18 when the flow meter 16 is oriented as intended for use. This is preferable in order to avoid problems with condensation in the vicinity of the ports of the pressure measurement channels 30, 32, which might otherwise negatively influence the pressure measurements. Other locations within the upper half of the tube 18 are also possible.

A pilot pressure chamber 34 is arranged adjacent to the outlet end of the outlet portion 22 and adjacent to the exhaust channel 28. The pilot pressure chamber is delimited by a pilot pressure chamber housing 35 and a flexible membrane 36, 56. In the pilot pressure chamber 34 a pilot pressure is applied. This pressure is varied according to the breathing cycle of the patient. The flexible membrane 36, 56 is arranged between the pilot pressure chamber 34 on the one side and the outlet of the outlet portion 22 and the exhaust channel 28 on the other side. On the other side, the pilot pressure chamber 34 is limited by the pilot pressure housing part 35. The flexible membrane may be a conventional membrane or a membrane 56 which is illustrated in detail in FIG. 6A, 6B, 7 and described in detail below. The flexible membrane 36, 56 is arranged to flex in and out of sealing engagement with the outlet end 22 in response to the amount and direction of the gas flow through the tube 18 and the pilot pressure, i.e., in response to the breathing of the patient.

Due to the pressure within the pilot pressure chamber 34, the membrane will be in sealing engagement, or at least located with only a minimum distance with the borders of the outlet end 22 of the tube 18, thereby closing off or limiting the fluid connection between the outlet portion 22 and the exhaust channel 28, when there is no flow through the flow meter 16, or when the pressure caused by the flow is not sufficient to push the membrane out of sealing engagement with the outlet 22. As the pressure caused by the flow increases above the pilot pressure, the membrane will flex towards the pilot pressure chamber 34, thereby allowing air flow, or an increased air flow, through the outlet portion 22 and the exhaust portion 28.

This is the basic design of the ventilator flow meter. According to some embodiments, the flow meter 16 may be provided with a turbulator 38, which will be described in detail below with reference to FIGS. 3A, 3B and 3C. According to some other embodiments, the flow meter may be provided with an improved flexible membrane 56, which will be described in detail below, and embodiments of which are schematically illustrated in FIGS. 6A and 6B, and in FIG. 7. However, preferably, as illustrated in FIGS. 2A and 2B, the ventilator flow meter 16 is provided with both the turbulator 38 and an improved membrane 56, in order to maximize measurement accuracy. Further, as will be described below with reference to FIG. 5, the membrane may be arranged such that an air flow escaping the outlet portion towards the exhaust channel is naturally guided to the largest part to flow with highest velocity in the tube regions most distant from the second measurement point P2.

In order to calculate the flow volume from the pressure measurements at points P1 and P2, an algorithm may be used. In this algorithm, it is assumed that the flow velocity profile and the pressure profile across the tube cross section are constant at both measurement points P1, P2. This is however, in most practical cases, a rough estimation, since in general flow meters are designed to achieve a laminar flow within the flow channel. According to prejudice, in order to get reasonable measurement accuracy, it is assumed that the flow through the venturi tube should be laminar. To the contrary, according to embodiments herein, the creation of turbulent flow in the venturi tube 18 has increased the measurement accuracy.

Therefore, a turbulator 38 is provided, which is arranged in the inlet portion 20. By this turbulator 38 a more homogeneous flow velocity profile across the tube cross section may be achieved, since the gas flow is spread out also to the inner walls of the tube 18. Thereby, a homogeneous flow velocity profile has been achieved at the pressure measurement points P1, P2.

Figure 3A:
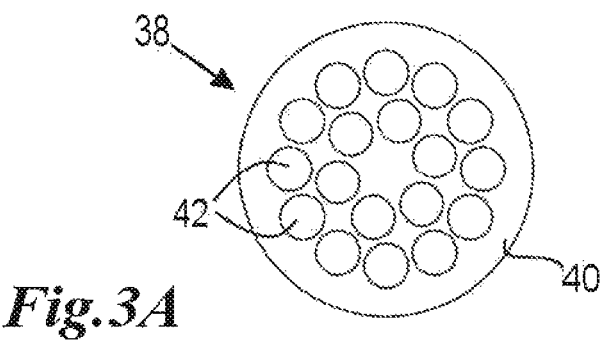
FIG. 3A illustrates one embodiment of the turbulator.

The turbulator 38 may be a plate 40 provided with a plurality of holes, or apertures 42, distributed across the plate 40, as illustrated in FIG. 3A. Although circular apertures are illustrated, in alternative embodiments the apertures may have other shapes, such as elliptical or polygonal. This plate 40 is arranged in the inlet portion 20, such that the incoming flow passes through the plate 40 whereby turbulence in the gas flow downstream of the turbulator is created by the plurality of apertures 42. The central part of the plate 40 may be solid, in order to create a uniform velocity profile and avoid a peak in velocity profile in the centre of the tube 18. The plate 40 is arranged such that it spans substantially the full cross section of the inlet portion 20. It has a diameter corresponding to the diameter d1 of the inlet portion 20 and is arranged perpendicularly to the inner walls thereof. Preferably it is arranged close to the entrance of the inlet portion 20, but at some distance from the entrance.

Figure 3B:
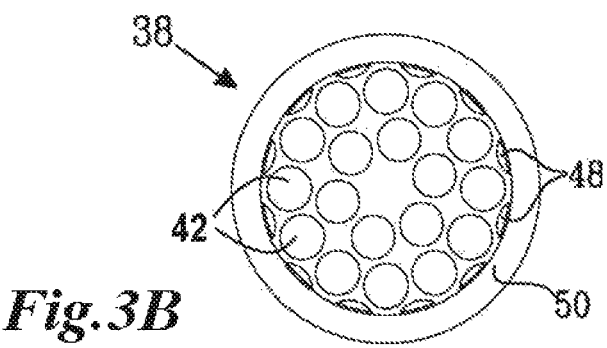
FIG. 3B, 3C illustrate another embodiment of the turbulator.
Figure 3C:
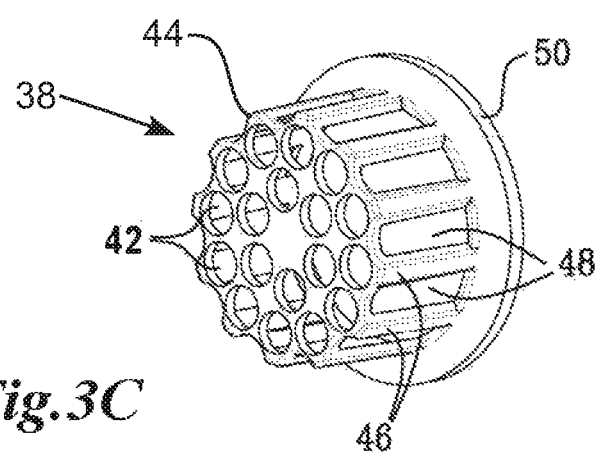

Alternatively, the turbulator 38 may comprise a hollow cylinder 44 having a cylinder wall 46 having a bottom provided with a plurality of apertures 42 and preferably being solid in the centre, such as the plate 40 described above. This is illustrated in FIGS. 3B and 3C. As can be seen, the cylinder wall 46 is also provided with holes, or apertures 48, preferably of elongated shape, such as to allow flow there through. The turbulator is dimensioned such that there is an annular space between the cylinder wall 46 and the inner wall of the inlet portion 20 where the turbulator 38 is positioned in the inlet portion 20, such as to allow air flow entering the flow meter also through the cylinder wall 46. The cylinder 44 may have a length such that the plate 40 is positioned at some distance from the opening of the inlet portion 20. Preferably, the cylinder 44 is provided with a radially protruding edge 50 or similar at the end opposite the plate 40, such as to keep the turbulator 44 in a proper place and prevent it from being pushed too far into the inlet portion 20.

The plate apertures 42, and the cylinder apertures 48 may be sized such as to prevent entry of undesired objects into the flow meter. Such undesired objects may for example be objects comprised in the exhaust air, for example caused by phlegm or mucus or aggregations of phlegm or mucus. The turbulator may thus have a dual function of creating a turbulent gas flow downstream of the turbulator, and of functioning as a sieve or filter in order to minimize, or at least to some degree avoid, contamination of the interior of the flow meter. The size of the apertures is preferably such that entry of undesired objects is efficiently prevented while at the same time the apertures should not become clogged too quickly. The turbulator may be removably arranged in the flow meter, and may be regularly replaced or cleaned.

Figure 4A:
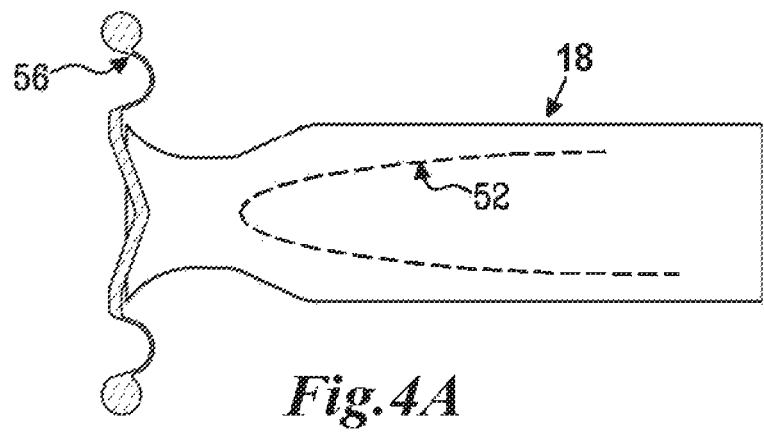
FIG. 4A illustrates a flow velocity profile in the absence of a turbulator.
Figure 4B:
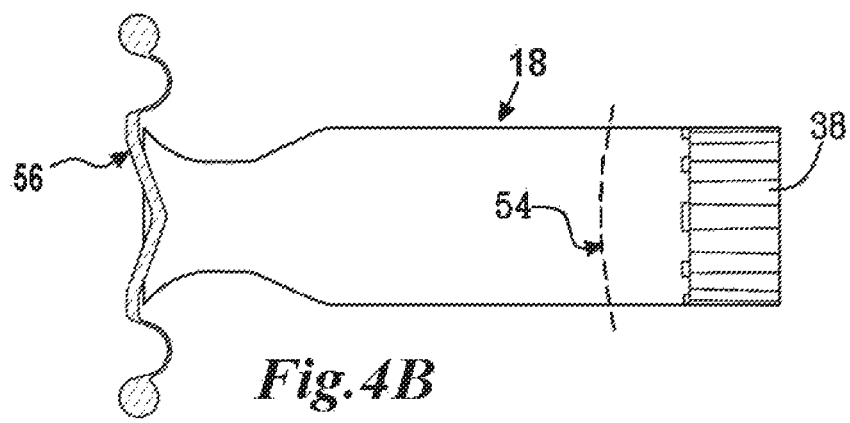
FIG. 4B illustrates a flow velocity profile in the presence of a turbulator.

FIG. 4A illustrates schematically a velocity profile 52 in the absence of a turbulator. As can be seen, the flow velocity is remarkably higher at the axial centre of the tube 20 than along the inner walls. In FIG. 4B the flow velocity profile 54 achieved under similar conditions but with a turbulator 44 in the inlet portion 20 is illustrated. As can be seen, the velocity profile 54 at some distance from the turbulator 44 is substantially uniform, or flat, across the tube cross section.

The presence of the turbulator 38, 40, 44 increases the pressure drop over the flow meter. However, the advantage of creating a more constant flow velocity profile outweighs the drawback of the increased flow resistance. These two parameters can be balanced against each other. Especially, the size of the apertures, and the number thereof, should be chosen such as to create a proper degree of turbulence while at the same time being large enough not to become clogged to easily. Also, the mechanical stability of the turbulator 38, 40, 44 should be considered. Additionally, the turbulator 38, 40, 44, due to its grid- or sieve-like structure in combination with its location close to the entrance of the flow meter additionally functions to prevent undesired objects from entering the flow meter. A common example of this is debris, for example phlegm or mucus, contained in the air exhausted by the patient. If this enters the flow sensor, it might cause errors in the measurement results. Further, due to the construction of the turbulator 38, 40, 44, it can be easily removed from the flow meter in order to be cleaned or replaced.

As mentioned above, the flow meter 16 comprises a flexible membrane for alternatingly flexing in and out of sealing engagement with the outlet tube portion 22 in response to variations in the gas flow entering the flow meter and the pressure in the pilot pressure chamber. This may be a membrane of a type conventionally used in venture type flow meters used in ventilators. However, the present invention provides for a membrane 56 with improved properties for this type of application.

Figure 5:
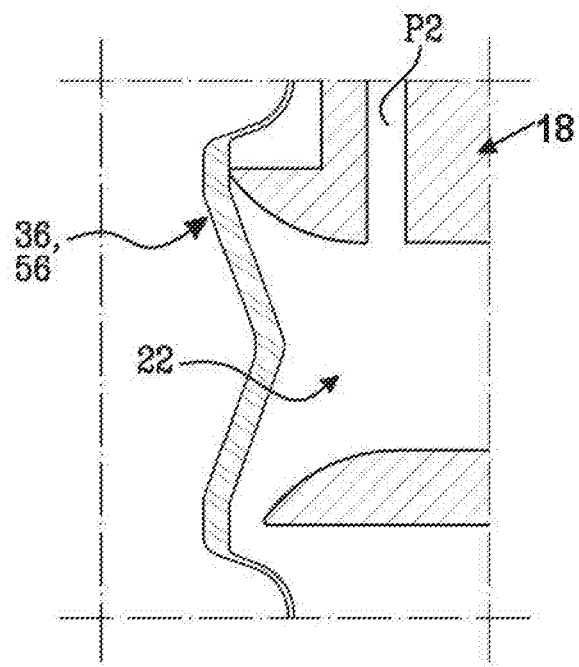
FIG. 5 illustrates a detail of a flow meter according to some preferred embodiments.
Figure 6A:
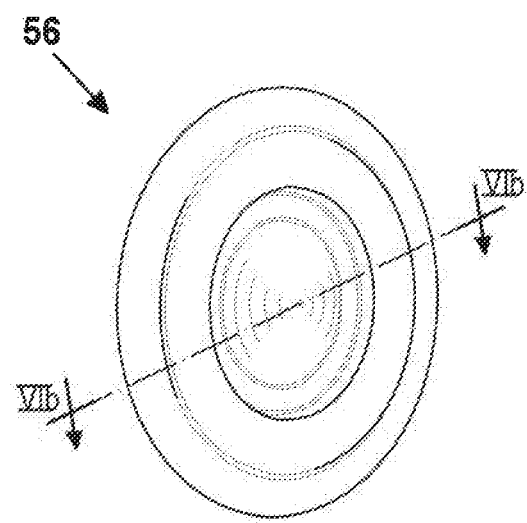
FIG. 6A illustrates a perspectivie view of a membrane according to some preferred embodiments.
Figure 6B:
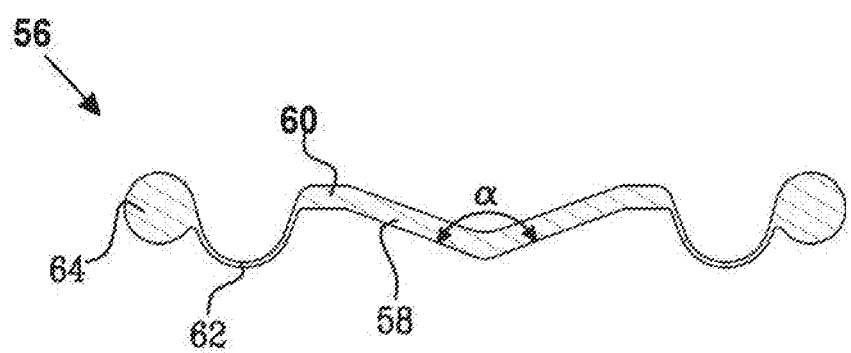
FIG. 6B illustrates a cross section of a membrane according to some preferred embodiments.

As illustrated in FIG. 5, this membrane 56 may be arranged such that the distance between the membrane, especially the seal section of the membrane, and the borders of the outlet portion 22 is not constant over the circumference of the outlet portion 22. The opening between the membrane seal section and the borders of the tube may have its largest value in a region of the seal section most distant from the second pressure measuring point P2. In the illustrated example, the second pressure measurement point P2 is located in the upper part of the tube 18. The membrane is arranged such that the largest opening between the membrane and the borders of the outlet portion 22 is provided in the lowest part of the outlet portion 22. Thereby, a gas flow through portion 22 is highest in the lower part of outlet portion 22. Thereby, problems with a pressure drop in the vicinity of the second pressure measurement point P2 are prevented, or at least decreased. This is especially important when the flow volumes are small.

The membrane 56, which will be described in detail here below, provides for faster response to flow variations and a higher degree of opening leading to decreased flow resistance through the flow meter. The membrane 56 is further designed to be resistant against natural frequency vibrations, which might otherwise give rise to disturbing acoustical noises. It should also be designed such that the influence of gravity upon the membrane is minimized, i.e., it should be stable in three dimensions when mounted in the flow meter, in order to provide for high accuracy of measurement results.

A membrane according to some preferred embodiments is illustrated in perspective view in FIG. 6A. A cross section of the membrane 56 taken along the line indicated by VIb is illustrated in FIG. 6B. At its centre, the membrane 56 has a cone shaped portion 58, with a substantially constant material thickness throughout the cone. In other words, the cone 58 is hollow and thereby relatively light weight. The cone shape contributes to by default flexing the membrane towards the outlet portion 22. However, alternatively, the central portion may be flat. The angle a is thereby less than or equal to 180°. The central portion 58 has a substantially flat rim portion. The dimension of this rim portion corresponds to the borders of the outlet portion 22, as can be seen in FIG. 2. Thereby, the flat rim portion forms a cone seal portion 60, adapted to seal against the borders of the outlet portion 22.

As can also be seen in FIG. 2B, the membrane is adapted to be mounted with the tip of the cone shaped portion 58 directed towards the outlet portion 22. Thereby, when the pressure in the tube 18 is lower than the pressure in the pilot pressure chamber 34, the cone seal portion 60 will be in sealing engagement with, or at least close to, the borders of the outlet portion 22. Further, due to the cone shape, the gas flow through the outlet portion 22 will be directed toward the edges thereof, and further toward the exhaust channel 28.

On its peripheral edge, the cone seal portion 60 is connected to a spring suspension portion 62, which in turn is connected to a peripheral seal section 64. As illustrated in FIG. 6B, the spring suspension portion 62 may comprise a thin, semi-circular section. The semi-circular section 62 is directed in the same direction as the cone shaped portion 58, such that, when mounted in the flow meter, the convex surface of the spring suspension portion 62 faces the exhaust channel 28. The peripheral seal section 64 is adapted to form the seal between the pilot pressure chamber 34 and the housing 26. The peripheral seal section 64 is thereby fixed in position with respect to the housing 26.

Due to this specific design, the membrane 56 provides for a fast response to variations in pressure difference over the membrane 56, which are caused by the periodic variations in gas flow provided by the ventilator 4. When the pressure in the pilot pressure chamber 34 is higher than the pressure in the outlet portion 22, the cone seal portion 60 efficiently seals against the borders of the outlet portion 22. When the pressure in the outlet portion 22 is higher than the pilot pressure, the membrane 56 flexes inwards towards the pilot pressure chamber 34 via a flexing movement, especially via the spring suspension portion 62. Thereby, the resulting flow passage between the outlet portion 22 and the exhaust channel 28 has a large cross section, and the flow resistance is low, thereby providing low flow resistance through the flow meter 16. The spring constant of the spring suspension portion 62 is selected such as to optimize the response properties of the membrane to flow variations.

In some embodiments, portions of the membrane, for example the spring suspension portion 62, may be provided with weights and/or with strengthening means, for example in the form of additional material at specific portions in order to minimize influence of gravity, and/or to function as balancing weights providing damping of natural frequency vibrations. Alternatively, strengthening ribs may be provided at specific locations on the membrane.

Figure 7:
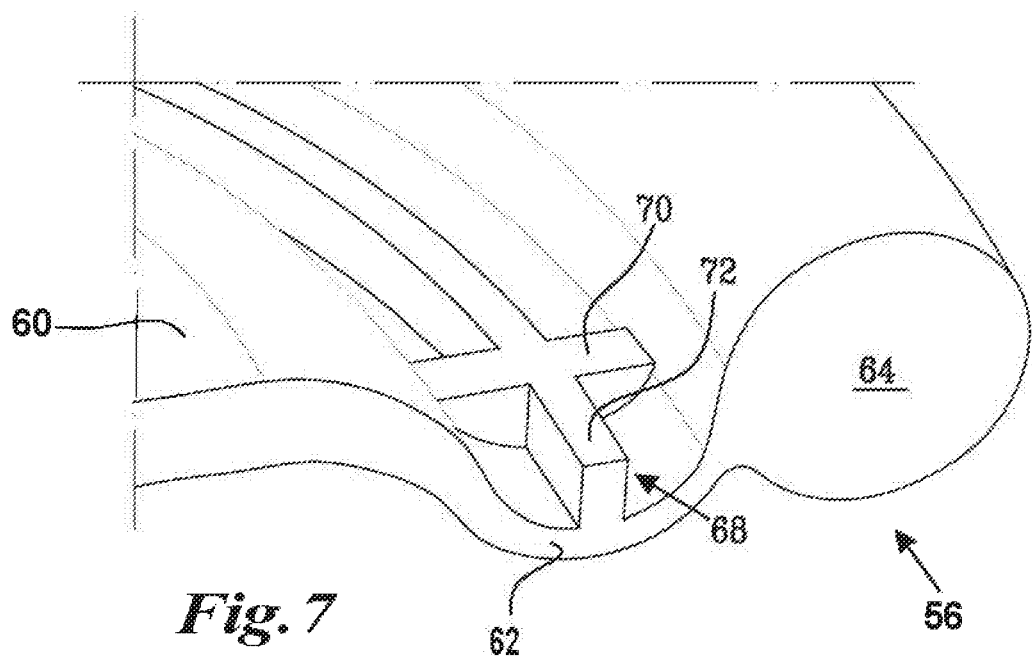
FIG. 7 illustrates a perspective view of a membrane according to some preferred embodiments.

A part of a membrane 56 provided with one example of such strengthening means 68 is illustrated in FIG. 7. Here, the strengthening means comprise one or more radially extending portions 70, which may be equally distributed throughout the spring suspension portion. The strengthening means 68 further comprise a ring-shaped element 72. The ring-shaped element 72 may be a closed ring, extending 360° throughout the spring suspension portion such as to enclose the central portion of the membrane. Alternatively, the element 72 may comprise a plurality of ring segments. The strengthening means are located within the concave part of the spring suspension means.

The membrane 56 may comprise a material having a low rebound value, which provides for high degree of damping of natural frequency vibrations, which may otherwise cause disturbing acoustic noise. Such a material may be a silicone material, especially a 752-elastocile material, having a rebound value of approximately 33%, and a Shore hardness in the range of 35 to 55, preferably 50 Shore. A too low Shore hardness value will increase the tendency of the membrane to stick or cling to adjacent surfaces thereby obstructing the response to the breathing of the patient. A too high Shore hardness value, on the other hand, leads to a slow response to pressure variations due to the resulting stiffness of the membrane. A too rigid membrane will also lead to inappropriate sealing.

The turbulator as described above could also be provided in a flow meter associated with the source of pressurized breathing gas in the ventilator 4.

The above mentioned and described embodiments are only given as examples and should not be limiting to the present invention. Other solutions, uses, objectives, and functions within the scope of the invention as claimed in the below described patent claims should be apparent for the person skilled in the art.

We claim:

1. A Flow meter comprising:
   a tube having an inlet portion having a first inner diameter, an outlet portion having a second inner diameter, and an intermediate portion having a third inner diameter which is smaller than both the first inner diameter and the second inner diameter; a first pressure measuring point located in the inlet portion and adjacent the intermediate portion;
   a second pressure measuring point located in the intermediate portion;
   wherein the tube is arranged in a housing, the housing having a flow exhaust channel in flow connection to an outlet end of the outlet portion, the flow exhaust channel at least partly surrounding the outlet portion; and
   a pilot pressure chamber arranged adjacent to the outlet end of the outlet portion and adjacent to the exhaust channel, wherein a flexible membrane is arranged between the pilot pressure chamber and the outlet end of the outlet portion and the exhaust channel;
   wherein the membrane comprises a central portion having a flat rim portion forming a seal portion which is peripherally connected to a peripheral seal section via a spring suspension portion,
   wherein the membrane is arranged such that the seal portion faces a border portion of the outlet end, the spring suspension portion faces the flow exhaust channel, and the peripheral seal is arranged in sealing engagement between the housing and the pilot pressure chamber; and
   wherein the membrane is arranged such that the distance between the seal portion and the border portion of the outlet end is largest in a portion of the outlet end most distant from the second pressure measurement point.

2. The Flow meter according to claim 1, wherein the membrane comprises a material having a rebound value lower than or equal to 35%.

3. The flow meter according to claim 1, wherein said spring suspension portion comprises strengthening means adapted to provide the suspension portion with a spring constant such as to prevent resonant oscillations of the flexible membrane.

4. The Flow meter according to any of claim 1, wherein the membrane is arranged such that an air flow resistance of a gas flow from the outlet end and into the flow exhaust channel will be lowest in a portion of the outlet end most distant from the second pressure measurement point.

5. A flexible membrane for use in a flow meter within a ventilator, wherein the membrane comprises:
   a central portion surrounded by a flat rim portion forming a seal portion which is peripherally connected to a peripheral seal section via a spring suspension portion surrounding the rim portion;
   wherein said spring suspension portion comprises strengthening means adapted to provide the suspension portion with a spring constant such as to prevent resonant oscillations of the flexible membrane.

6. The Flexible membrane according to claim 5 comprising a material having a rebound value lower than or equal to 35%.

7. A flow meter comprising:
   a tube having an inlet portion having a first inner diameter, an outlet portion having a second inner diameter, and an intermediate portion having a third inner diameter which is smaller than both the first inner diameter and the second inner diameter; a first pressure measuring point located in the inlet portion and adjacent the intermediate portion;
   a second pressure measuring point located in the intermediate portion;
   wherein the tube is arranged in a housing, the housing having a flow exhaust channel in flow connection to an outlet end of the outlet portion, the exhaust channel at least partly surrounding the outlet portion; and
   a pilot pressure chamber arranged adjacent to the outlet of the outlet portion and adjacent to the flow exhaust channel, wherein a flexible membrane is arranged between the pilot pressure chamber and the outlet of the outlet portion and the exhaust channel,
   wherein the membrane is arranged such that the central portion faces the outlet, the seal section faces a border portion of the outlet, the spring suspension portion faces the flow exhaust channel, and the peripheral seal is arranged in sealing engagement between the housing and the pilot pressure chamber.

8. The Flow meter according to claim 7, wherein the membrane comprises a material having a rebound value lower than or equal to 35%.

9. The Flow meter according to claim 7, wherein the membrane is arranged such that an air flow resistance of a gas flow from the outlet end and into the exhaust channel will be lowest in a portion of the outlet end most distant from the second pressure measurement point.

10. The Flow meter according to any of claim 7, wherein the membrane is arranged such that the distance between the seal portion and the portion of the outlet end is not constant throughout a circumference of the border portion.

* * * * *